(12) United States Patent
Borlongan et al.

(10) Patent No.: US 9,828,593 B2
(45) Date of Patent: Nov. 28, 2017

(54) METHODS AND COMPOSITIONS FOR TREATMENT OF TRAUMATIC BRAIN INJURY AND FOR MODULATION OF MIGRATION OF NEUROGENIC CELLS

(71) Applicants: SanBio, Inc., Mountain View, CA (US); University of South Florida, Tampa, FL (US)

(72) Inventors: Cesar V. Borlongan, Tampa, FL (US); Casey C. Case, San Mateo, CA (US)

(73) Assignees: SanBio, Inc., Mountain View, CA (US); University of South Florida, Tampa, FL (US)

(*) Notice: Subject to any disclaimer, the term of this patent is extended or adjusted under 35 U.S.C. 154(b) by 0 days.

(21) Appl. No.: 13/800,585

(22) Filed: Mar. 13, 2013

(65) Prior Publication Data

US 2014/0186316 A1 Jul. 3, 2014

Related U.S. Application Data

(60) Provisional application No. 61/647,893, filed on May 16, 2012.

(51) Int. Cl.
| | |
|---|---|
| *A61K 35/28* | (2015.01) |
| *A61K 9/00* | (2006.01) |
| *C12N 9/64* | (2006.01) |
| *C12N 5/079* | (2010.01) |

(52) U.S. Cl.
CPC .......... *C12N 9/6491* (2013.01); *A61K 9/0085* (2013.01); *A61K 35/28* (2013.01); *C12N 5/0618* (2013.01); *C12N 2501/42* (2013.01); *C12N 2506/1353* (2013.01); *C12N 2510/00* (2013.01); *C12Y 304/24035* (2013.01)

(58) Field of Classification Search
None
See application file for complete search history.

(56) References Cited

U.S. PATENT DOCUMENTS

| | | | |
|---|---|---|---|
| 5,486,359 | A | 1/1996 | Caplan et al. |
| 6,989,271 | B2 | 1/2006 | Dezawa et al. |
| 7,682,825 | B2 | 3/2010 | Dezawa et al. |
| 8,092,792 | B2 | 1/2012 | Dezawa et al. |
| 8,133,725 | B2 | 3/2012 | Dezawa et al. |
| 8,361,456 | B2 | 1/2013 | Dezawa et al. |
| 8,785,190 | B2 | 7/2014 | Dao et al. |
| 8,945,919 | B2 | 2/2015 | Mori et al. |
| 2003/0003090 | A1 | 1/2003 | Prockop et al. |
| 2006/0216276 | A1 | 9/2006 | Dezawa et al. |
| 2010/0266554 | A1 | 10/2010 | Mori et al. |
| 2010/0310529 | A1 | 12/2010 | Aizman |
| 2011/0136114 | A1 | 6/2011 | Case |
| 2011/0229442 | A1 | 9/2011 | Dezawa |
| 2011/0306137 | A1 | 12/2011 | Aizman |
| 2012/0263681 | A1 | 10/2012 | Miyoshi et al. |
| 2013/0071924 | A1 | 3/2013 | Dezawa |
| 2013/0195817 | A1 | 8/2013 | Dao et al. |
| 2013/0210000 | A1 | 8/2013 | Aizman et al. |
| 2014/0286918 | A1 | 9/2014 | Dao et al. |
| 2014/0363408 | A1 | 12/2014 | Aizman |
| 2015/0197741 | A1 | 7/2015 | Borlongan et al. |

FOREIGN PATENT DOCUMENTS

| | | |
|---|---|---|
| EP | 1 479 767 A1 | 11/2004 |
| WO | WO 2004/110387 | 12/2004 |
| WO | WO 05/100552 A2 | 10/2005 |
| WO | WO 2008/102460 A1 | 8/2008 |
| WO | WO 09/023251 A1 | 2/2009 |
| WO | WO 2013/172944 | 11/2013 |

OTHER PUBLICATIONS

Bramlett et al. Journal of Cerebral Blood Flow & Metabolism (2004) 24, 133-150.*
Leker et al. Brain Res Brain Res Rev. Jun. 2002;39(1):55-73.*
Favory et al., Journal of Neurotrauma. Jun. 2010, 27(5): A-7, abstract #15.*
Aizman, et al., "Extracellular Matrix Produced by Bone Marrow Stromal Cells and by Their Derivative, SB623 Cells, Supports Neural Cell Growth," *J. Neuroscience Research* 87:3198-3206 (2009).
Aizman, et al. "Quantitative Microplate Assay for Studying Mesenchymal Stromal Cell-Induced Neuropoiesis," *Stem Cells Translational Medicine* 2:223-232 (2013).
Ali, et al., "Notch-Induced Human Bone Marrow Stromal Cell Grafts Express Neuronal Phenotypic Markers and Reduce Ischemic Cell Loss in Tandem With Behavioral Recovery of Transplanted Stroke Animals," *Cell Transplantation* 17:458 (2008).
Dao, et al., "Comparing the Immunosuppressive Potency of Naïve Marrow Stromal Cells and Notch-Transfected Marrow Stromal Cells," *J. Neuroinflammation* 8:133-146 (2011).

(Continued)

*Primary Examiner* — James D Schultz
(74) *Attorney, Agent, or Firm* — Levine Bagade Han LLP

(57) ABSTRACT

Disclosed herein are methods for the treatment of traumatic brain injury by transplantation of cells descended from marrow adherent stem cells that express an exogenous Notch intracellular domain. The transplanted cells form a pathway along which endogenous neurogenic cells proliferate and migrate from the subventricular zone to the site of injury.

20 Claims, 7 Drawing Sheets

(56) References Cited

OTHER PUBLICATIONS

Dao, et al., "Comparing the Angiogenic Potency of Naïve Marrow Stromal Cells and Notch-Transfected Marrow Stromal Cells," *J. Translational Medicine* 11:81-91 (2013).
Dezawa, "Transdifferentiation of Bone Marrow Stromal Cells to Neural Cells and Application to Stem Cell Therapy," *Acta Anatomica Nipponica* 78suppl:97 (Abstract S04-6) (2003).
Dezawa, et al., "Treatment of Neurodegenerative Diseases Using Adult Bone Marrow Stromal Cell-Derived Neurons," *Expert Opinion Biol. Therapy* 5:427-435 (2005).
Glasvaski-Joksimovic, et al., "Glial Cell Line-Derived Neurotrophic Factor-Secreting Genetically Modified Human Bone Marrow-Derived Mesenchymal Stem Cells Promote Recovery in a Rat Model of Parkinson's Disease," *Cell Transplantation* 18:801-814 (2009).
Harvey, et al., "Proteomic Analysis of the Extracellular Matrix Produced by Mesenchymal Stromal Cells: Implications for Cell Therapy Mechanism," *PLOS ONE* 8(11):e79283 (2013).
Tajiri, et al., "Stem Cell Recruitment of Newly Formed Host Cells Via a Successful Seduction? Filling the Gap Between Neurogenic Niche and Injured Brain Site," *PLOS ONE* 8(9):e74857 (2013).
Tate, et al., "Abstracts for the 11th International Neural Transplantation and Repair Meeting Held in Conjunction With the 18th Annual Meeting of The American Society for Neural Therapy and Repair," *Cell Transplantation* 20:588 (2011).
Tate, C.C. and Case, C.C., *Transplanted Mesenchymal Stem Cells Aid the Injured Brain through Trophic Support Mechanisms*, "Stem Cells and Cancer Stem Cells, vol. 4", M.A. Hayat (Ed), 297-304 (2012).
Tate, C.C. and Case, C.C., *Mesenchymal Stromal Cells to Treat Brain Injury*, "Advanced Topics in Neurological Disorders," K. S. Chen (Ed), 45-78 (2012).
Xu, et al., "Transplantation of Neuronal Cells Induced From Human Mesenchymal Stem Cells Improves Neurological Functions Afterstroke Without Cell Fusion," *J. Neuroscience Research* 88:3598-3609 (2010).
Office Action dated Aug. 23, 2013 in co-owned U.S. Appl. No. 13/441,311.
Andres, R. H. et al., "Human Neural Stem Cells Enhance Structural Plasticity and Axonal Transport in the Ischaemic Brain," *Brain* 134:1777-1789 (2011).
Artavanis-Tsakonas, et al., "Notch Signaling," *Science* 268(5208):225-232 (1995).
Barha, C. K. et al ,"Progesterone Treatment Normalizes the Levels of Cell Proliferation and Cell Death in the Dentate Gyrus of the Hippocampus After Traumatic Brain Injury," *Exp. Neurol.* 231:72-81 (2011).
Borlongan, C. V. "Bone Marrow Stem Cell Mobilization in Stroke: A 'Bonehead' May Be Good After All!" *Leukemia* 25:1674-1686 (2011).
Borlongan, C.V. et al., "Central Nervous System Entry of Peripherally Injected Umbilical Cord Blood Cells Is Not Required for Neuroprotection in Stroke," *Stroke* 35:2385-2389 (2004).
Campagnoli, et al., "Identification of Mesenchymal Stem/Progenitor Cells in Human First-Trimester Fetal Blood, Liver, and Bone Marrow," *Blood* 98(8):2396-2402 (2001).
Carlén, M. et al., "Forebrain Ependymal Cells Are Notch-Dependent and Generate Neuroblasts and Astrocytes After Stroke," *Nat. Neurosci.* 12:259-267 (2009).
del Amo, F., et al., "Cloning, Analysis and Chromosomal Localization of Notch-1, A Mouse Homolog of *Drosophilia* Notch," *Genomics* 15:259-264 (1993).
Dezawa, et al., "Sciatic Nerve Regeneration in Rats Induced by Transplantation of In Vitro Differentiated Bone-Marrow Stromal Cells," *Eur. J. Neurosci.* 14(11):1771-1776 (2001).
Dezawa, et al., "Specific Induction of Neuronal Cells From Bone Marrow Stromal Cells and Application for Autologous Transplantation," *Journal of Clinical Investigation* 113:1701-1710 (2004).
Ehebauer, et al., "Notch Signaling Pathway," *Sci. STKE* 2006(364):cm7 (2006) DOI:10.1126/stke.3642006cm71.
Erices, et al., "Mesenchymal Progenitor Cells in Human Umbilical Cord Blood," *Br. J. Haematol.* 109(1):235-242 (2000).
Espina, et al., "Laser-Capture Microdissection," *Nature Protoc.* 1:586-603 (2006).
GenBank Accession No. CAB40733 (Apr. 15, 2005).
Hargus, G. et al., "Differentiated Parkinson Patient-Derived Induced Pluripotent Stem Cells Grow in the Adult Rodent Brain and Reduce Motor Asymmetry in Parkinsonian Rats," *Proc. Natl. Acad. Sci. U. S. A.* 107:15921-15926 (2010).
Hong, S. H. et al., "Cell Fate Potential of Human Pluripotent Stem Cells is Encoded by Histone Modifications," *Cell Stem Cell* 9:24-36 (2011).
Hou, et al., "Induction of Umbilical Cord Blood Mesenchymal Stem Cells Into Neuron-Like Cells In Vitro," *Int. J. Hematol.* 78(3):256-261 (2003).
Jaskelioff, M. et al., "Telomerase Reactivation Reverses Tissue Degeneration in Aged Telomerase-Deficient Mice," *Nature* 469:102-106 (2011).
Jiang, et al., "Pluripotency of Mesenchymal Stem Cells Derived From Adult Marrow," *Nature* 418:41-49 (2002).
Joyner, et al., "Production of a Mutation in Mouse En-2 Gene by Homologous Recombination in Embryonic Stem Cells," *Nature* 338:153-156 (1989).
Kim, Y. et al., "Mouse B-Type Lamins Are Required for Proper Organogenesis But Not by Embryonic Stem Cells," *Science* 334:1706-1710 (2011).
Lee, H. S. et al., "FOXA2 and NURR1 Synergistically Yield A9 Nigral Dopamine Neurons Exhibiting Improved Differentiation, Function, and Cell Survival," *Stem Cells* 28:501-512 (2010).
Lee, J. P. et al., "Stem Cells Act Through Multiple Mechanisms to Benefit Mice With Neurodegenerative Metabolic Disease," *Nat. Med.* 13:439-447 (2007).
Liu, Z. et al., "Bone Marrow Stromal Cells Promote Skilled Motor Recovery and Enhance Contralesional Axonal Connections After Ischemic Stroke in Adult Mice," *Stroke* 42:740-744 (2011).
Lu, et al., "Intraarterial Administration of Marrow Stromal Cells in a Rat Model of Traumatic Brain Injury," *J. Neurotrauma* 18:813-819 (2001).
Ma, D. K. et al., "Epigenetic Choreographers of Neurogenesis in the Adult Mammalian Brain," *Nat. Neurosci.* 13:1338-1344 (2010).
Mazzocchi-Jones, D. et al., "Embryonic Striatal Grafts Restore Bi-Directional Synaptic Plasticity in a Rodent Model of Huntington's Disease," *Eur. J. Neurosci.* 30:2134-2142 (2009).
Mezey, E. "The Therapeutic Potential of Bone Marrow-Derived Stem Cells," *J. Cell. Biochem.* 112:2683-2687 (2011).
Mumm, et al., "Notch Signaling: From the Outside in," *Dev. Biol.* 228(2):151-165 (2000).
NCBI Reference Sequence No. NM_017167 (Apr. 29, 2013).
Pastori, C. et al., "Arterially Perfused Neurosphere-Derived Cells Distribute Outside the Ischemic Core in a Model of Transient Focal Ischemia and Reperfusion In Vitro," *Plos One* 3(7): E2754 (2008).
Pittenger, et al., "Multilineage Potential of Adult Human Mesenchymal Stem Cells," *Science* 284(5411):143-147 (1999).
Pollock, K. et al., "A Conditionally Immortal Clonal Stem Cell Line Form Human Cortical Neuroepithelium for the Treatment of Ischemic Stroke," *Exp. Neurol.* 199:143-155 (2006).
Prockop, et al., "Marrow Stromal Cells As Stem Cells for Nonhematopoietic Tissues," *Science* 276(5309):71-74 (1997).
Redmond, D. E. Jr. et al., "Behavioral Improvement in a Primate Parkinson's Model is Associated With Multiple Homeostatic Effects of Human Neural Stem Cells," *Proc. Natl. Acad. Sci. U. S. A.* 104:12175-12180 (2007).
Robel, S. et al., "The Stem Cell Potential of a Glia: Lessons From Reactive Gliosis," *Nat. Rev. Neurosci.* 12:88-104 (2011).
Sanai, N. et al., "Corridors of Migrating Neurons in the Human Brain and Their Decline During Infancy," *Nature* 478:382-386 (2011).
Seol, H. J. et al., "Genetically Engineered Human Neutral Stem Cells With Rabbit Carboxyl Esterase Can Target Brain Metastasis From Breast Cancer," *Cancer Lett.* 311:152-159 (2011).
SwissProt P46531 (Nov. 1, 1995).
SwissProt Q01705 (Nov. 1, 1995).

(56) References Cited

OTHER PUBLICATIONS

Tate, et al., "Human Mesenchymal Stromal Cells and Their Derivative, SB623 Cells, Rescue Neural Cells Via Trophic Support Following In Vitro Ischemia," *Cell Transplant* 19(8):973-984.

Wang, L. et al., "Tumor Necrosis Factor a Primes Cerebral Endothelial Cells for Erythropietin-Induced Andiogenesis," *J. Cereb. Blood Flow Metab.* 31:640-647 (2011).

Yasuda, A. et al., "Significance of Remyelination by Neural Stem/ Progenitor Cells Transplanted Into the Injured Spinal Cord," *Stem Cells* 29:1983-1994 (2011).

Yasuhara, T. et al., "Transplantation of Human Neural Stem Cells Exerts Neuroprotection in a Rat Model of Parkinson's Disease," *J. Neurosci.* 26:12497-12511 (2006).

Yasuhara, T. et al. "Intravenous Grafts Recapitulate the Neurorestoration Afforded by Intracerebrally Delivered Multipotent Adult Progenitor Cells in Neonatal Hypoxic-Ischemic Rats," *J. Cereb. Blood Flow Metab.* 28:1804-1810 (2008).

Yasuhara, T. et al., "Notch-Induced Rat and Human Bone Marrow Stromal Cell Grafts Reduce Ischemic Cell Loss and Ameliorate Behavioral Deficits in Chronic Stroke Animals," *Stem Cells Dev.* 18:1501-1514 (2009).

Zhao, B.Q. et al., "Role of Matrix Metalloproteinases in Delayed Cortical Responses After Stroke," *Nat Med.* 12:441-445 (2006).

Zhao, B.Q., Tejima, E., Lo, E.H. "Neurovascular Proteases in Brain Injury, Hemorrhage and Remodeling After Stroke," *Stroke* 38:748-752 (2007).

Asahi, Minoru et al., "Effects of Matrix Metalloproteinase-9 Gene Knock-Out on the Proteolysis of Blood—Brain Barrier and White Matter Components after Cerebral Ischemia," *J. Neurosci*, 21(19):7724-7732, Oct. 1, 2001.

Asahi, Minoru et al., "Role for Matrix Metalloproteinase 9 After Focal Cerebral Ischemia: Effects of Gene Knockout and Enzyme Inhibition With BB-94," *J. Cereb. Blood Flow Metab.*, 20(12):1681-1689, 2000.

Lee et al., "Involvement of Matrix Metalloproteinase in Neuroblast Cell Migration from the Subventricular Zone after Stroke," *J. Neurosci*, 26(13):3491-3495 (2006).

Wang, Xiaoying, "Effects of Matrix Metalloproteinase-9 Gene Knock-Out on Morphological and Motor Outcomes after Traumatic Brain Injury," *J. Neurosci.*, 20(18):7037-7042, Sep. 15, 2000.

Wang, Xiaoying, "Lipoprotein receptor-mediated induction of matrix metalloproteinase by tissue plasminogen activator," *Nature Medicine*, 9(10):1313-1317, Oct. 2003.

364205 GM 6001—CAS 142880-36-2—Calbiochem, http://www.emdmillipore.com/US/en/product/GM-6001---CAS-142880-36-2---Calbiohem,EMD_BIO-364205?bd=1 visited Aug. 4, 2015.

GM-6001 BML E1300—Enzo Life Sciences, http://www.enzolifesciences.com/BML-EI300/gm-6001/ visited Aug. 4, 2015.

Favory, Austin M., "Transplantation of Neurospheres Derived from Genetically Modified Adult Bone Marrow Stromal Cells Following a Controlled Cortical Impact (CCI): Effects on Transplant Survival and Behavioral Recovery" (2014). College of Science and Health Theses and Dissertations. Paper 86. http://via.library.depaul.edu/csh_etd/86.

Cesarz, Zoe et al., "Spheroid Culture of Mesenchymal Stem Cells", Stem Cells International, vol. 2016, Article ID 9176357; 11 pages, http://dx.doi.org/10.1155/2016/9176357.

\* cited by examiner

A

B

METHODS AND COMPOSITIONS FOR TREATMENT OF TRAUMATIC BRAIN INJURY AND FOR MODULATION OF MIGRATION OF NEUROGENIC CELLS

CROSS REFERENCE TO RELATED APPLICATIONS

This application claims the benefit of U.S. provisional patent application No. 61/647,893, filed May 16, 2012; the specification and drawings of which are incorporated herein by reference in their entireties for all purposes.

STATEMENT REGARDING FEDERAL SUPPORT

Some of the research described herein was supported by a grant from the National Institute of Neurological Disorders and Stroke. The United States government may have certain rights in the inventions disclosed herein.

FIELD

The present disclosure is in the field of cell therapy for neurological disorders.

BACKGROUND

Initially employed for in-depth examination of cell development[1], stem cells have become a cornerstone for regenerative medicine, including cell-based therapies for treatment of neurological disorders[2,3]. Stem cells exist even in adulthood[8], and possess the capacity to self-renew and differentiate into multiple lineages[9], contribute to normal homeostasis[10], and exert therapeutic benefits either endogenously[11-14] or following transplantation in injured organs, i.e., brain[15-21]. The subventricular zone (SVZ) of the lateral ventricles and the subgranular zone of the hippocampus dentate gyrus are the two major stem-cell niches in the adult brain[22,23], although quiescent neural stem cells (NSCs) have been detected in other brain regions[24]. Induction of endogenous stem cells after injury would provide new opportunities in regenerative medicine[2,3,11-21].

Cells other than pluripotent stem cells have also been used in the treatment of disorders of the central nervous system. As one example, SB623 cells (which are cells derived from marrow adherent stem cells in which an exogenous Notch intracellular domain has been expressed) are used for the treatment of stroke, by transplantation at or near the site of ischemic insult. See, for example, U.S. Pat. No. 8,092,792 and Yasuhara et al. (2009) *Stem Cells Devel.* 18:1501-1513. U.S. Pat. No. 7,682,825 describes additional uses of SB623 cells in the treatment of a number of disorders of the central and peripheral nervous systems.

Despite these scientific advances and some initial clinical studies[25-27], a fundamental gap in our understanding of cell therapy is a knowledge of the mechanisms by which transplanted cells facilitate the repair of damaged neural tissue. To date, increased graft survival and graft persistence have been considered the crux of successful cell transplantation therapy in affording therapeutic benefits in hematologic and non-hematologic disorders. Thus, much effort has been directed to prolonging the survival and persistence of transplanted cells. Accordingly, methods for effective cell therapy, that do not require the persistence of large amounts of transplanted cells, would be advantageous.

Traumatic brain injury (TBI) refers to damage to the brain resulting from external mechanical force. TBI can result from falls, firearm wounds, sports accidents, construction accidents and vehicle accidents, among other causes. Victims of TBI can suffer from a number of physical, cognitive, social, emotional and/or behavioral disorders.

Little can be done to reverse the initial physical damage of a TBI. Therefore, treatment options consist primarily of stabilization to prevent further damage in the acute phase, and rehabilitation thereafter. Because of these limited options, additional methods and compositions for treatment of TBI are needed.

SUMMARY

The present inventors have discovered that transplantation of SB623 cells (i.e., cells derived from marrow adherent stem cells in which an exogenous Notch intracellular domain has been expressed) can be used in the treatment of traumatic brain injury (TBI). Animals that received transplants of SB623 cells after TBI displayed significantly improved motor and neurological functions coupled with significantly reduced damage to the cortical core and peri-injured cortical areas, compared to traumatically injured animals that received injection of vehicle only.

The inventors have also found that, contrary to expectations, survival and persistence of large numbers of transplanted cells are not required for the therapeutic benefits of SB623 cell transplantation. Surprisingly, therapeutic benefits can be obtained by minimum and acute graft survival, which is sufficient to initiate a robust and stable functional recovery. This solves two major problems: the need for an ample supply of transplantable cells and the need for long-term graft survival.

The inventors have also discovered that the beneficial effects of SB623 cell transplantation, in the treatment of TBI, result from the formation of a biological bridge ("biobridge") between the neurogenic niche in the subventricular zone (SVZ) and the injured brain site. This biobridge, which has been visualized immunohistochemically and laser-captured, initially expressed high levels of extracellular matrix metalloproteinases and was characterized by a stream of the transplanted cells. At later times after transplantation, the grafted cells were replaced by newly formed host cells, and few-to-no transplanted cells remained in the biobridge. Thus, the transplanted SB623 cells initially formed a pathway between the neurogenic SVZ and the injured cortex that facilitated later migration of host neurogenic cells from the neurogenic niche to the site of brain injury.

This sequence of events reveals a novel method for treatment of TBI; namely, transplantation of SB623 cells, which form transient pathways for directing the migration of host neurogenic cells. That is, the transplanted SB623 cells initially form a biobridge between a neurogenic niche and the site of injury; but once this biobridge is formed, the grafted cells are replaced by host neurogenic cells which migrate to the injury site. These findings reveal that long-distance migration of host cells from a neurogenic niche to an injured brain site can be achieved through transplanted SB623 cells serving as biobridges for initiation of endogenous repair mechanisms.

Accordingly, the present disclosure provides, inter alia, the following embodiments:

1. A method for treating traumatic brain injury in a subject, the method comprising administering, to the brain of the subject, a therapeutically effective amount of SB623 cells, wherein the SB623 cells are obtained by (a) providing a culture of marrow adherent stem cells (MSCs), (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

2. The method of embodiment 1, wherein the subject is a human.

3. The method of either of embodiments 1 or 2, wherein the MSCs are obtained from a human.

4. Cells for transplantation into a subject for the treatment of traumatic brain injury, wherein said cells are obtained by a process comprising the steps of: (a) providing a culture of MSCs, (b) contacting the cell culture of step (a) with a polynucleotide comprising sequences encoding a NICD wherein said polynucleotide does not encode a full-length Notch protein, (c) selecting cells that comprise the polynucleotide of step (b), and (d) further culturing the selected cells of step (c) in the absence of selection.

5. The cells of embodiment 4, wherein the subject is a human.

6. The cells of either of embodiments 4 or 5, wherein the MSCs are obtained from a human.

7. A method for inducing the migration of endogenous neurogenic cells from a neurogenic niche to a site of brain injury, the method comprising administering, to the brain of a subject, a therapeutically effective amount of SB623 cells, wherein the SB623 cells are obtained by (a) providing a culture of MSCs, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

8. The method of embodiment 7, wherein the neurogenic niche is the subventricular zone.

9. The method of either of embodiments 7 or 8, wherein the brain injury is a traumatic brain injury.

10. The method of any of embodiments 7-9, wherein the subject is a human.

11. The method of any of embodiments 7-10, wherein the MSCs are obtained from a human.

12. A method for stimulating proliferation of neurogenic cells in a subject, the method comprising administering, to the brain of a subject, a therapeutically effective amount of SB623 cells, wherein the SB623 cells are obtained by (a) providing a culture of MSCs, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

13. The method of embodiment 12, wherein the brain injury is a traumatic brain injury.

14. The method of either of embodiments 12 or 13, wherein the subject is a human.

15. The method of any of embodiments 12-14, wherein the MSCs are obtained from a human.

16. A method for inducing neurogenic cells to proliferate and migrate to a site of brain injury in a subject, the method comprising administering, to the brain of a subject, a therapeutically effective amount of SB623 cells, wherein the SB623 cells are obtained by (a) providing a culture of MSCs, (b) contacting the cell culture of step (a) with a polynucleotide comprising sequences encoding a Notch intracellular domain (NICD) wherein said polynucleotide does not encode a full-length Notch protein, (c) selecting cells that comprise the polynucleotide of step (b), and (d) further culturing the selected cells of step (c) in the absence of selection.

17. The method of embodiment 16, wherein the brain injury is a traumatic brain injury.

18. The method of either of embodiments 16 or 17, wherein the subject is a human.

19. The method of any of embodiments 16-18, wherein the MSCs are obtained from a human.

BRIEF DESCRIPTION OF THE DRAWINGS

FIG. 4A shows H&E sections of brains from rats that received transplants of SB623 cells (panels a-d) compared to rats that received infusion of vehicle (panels a1-d1). In FIG. 4B, the results are expressed as percent lesioned area (see Example 8) relative to animals subjected to TBI that received infusion of vehicle. The left-most bar in each pair shows values for the core region; the right-most bar in each pair shows values for the peri-injury region.

"*" indicates a statistically significant increase in the number of labeled cell observed per high-power field (p<0.05).

Figure 7:
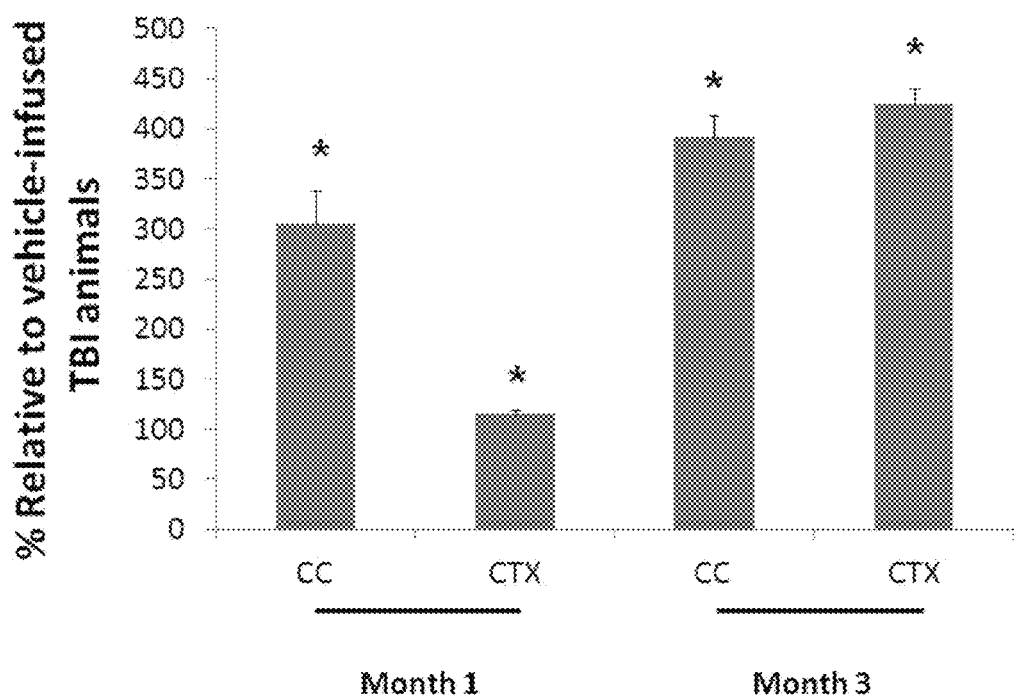

FIG. 7 shows levels of doublecortin-labeled cells in the corpus callosum ("CC") and the cortex ("CTX") of animals subjected to TBI that received transplants of SB623 cells, compared to animals subjected to TBI that received infusions of vehicle, at one month and three months after TBI. "*" indicates a statistically significant increase in the number of labeled cell observed per high-power field (p<0.05).

Figure 8:
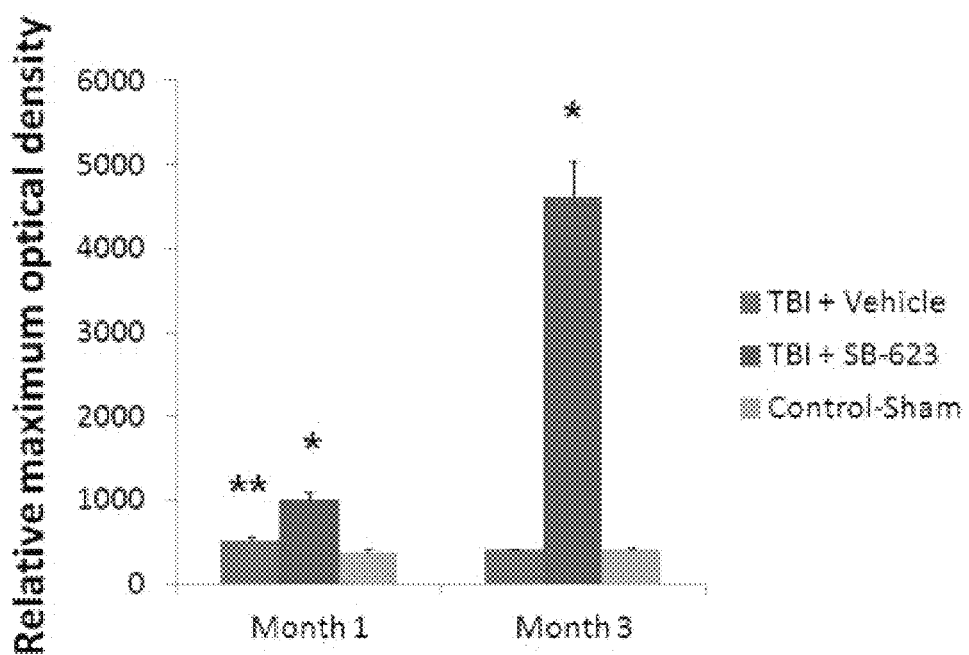

FIG. 8 shows lytic activity in homogenates of laser-captured biobridges from the brains of rats subjected to experimental TBI, at one month and three months after TBI. Activities are expressed as optical density units, relative to 0.5 ng recombinant MMP-9, obtained by scanning zymographic gels. In each of the two sets of three bars, the left-most bar represents relative activity in biobridges from rats infused with vehicle after TBI, the center bar represents relative activity in biobridges from rats transplanted with SB623 cells after TBI, and the right-most bar represents relative activity in biobridges from control, sham-operated rats.

DETAILED DESCRIPTION

Disclosed herein are methods and compositions for treatment of traumatic brain injury (TBI). Also disclosed herein are methods and compositions for modulation of the migration of stem cells (e.g., neural stem cells, neuronal stem cells) in the brain.

The inventors have made the surprising discovery that the behavioral and histological improvements resulting from cell transplantation, after TBI, do not require large-scale graft survival or long-term graft persistence. Indeed, only modest, acute graft survival is necessary to produce these therapeutic benefits. Thus, the inventors have uncovered a novel method for neural repair that entails a threshold dose of transplanted cells, which do not need to persist in the brain, and which are capable of inducing the SVZ to generate and propel new cells to the impacted cortical area. Accordingly, transplanting the minimum effective dose and the acute survival of the transplanted cells are sufficient to initiate an intricate endogenous restorative machinery for abrogating a massive brain injury.

Practice of the present disclosure employs, unless otherwise indicated, standard methods and conventional techniques in the fields of cell biology, toxicology, molecular biology, biochemistry, cell culture, immunology, neurology, surgery, recombinant DNA and related fields as are within the skill of the art. Such techniques are described in the literature and thereby available to those of skill in the art. See, for example, Alberts, B. et al., "Molecular Biology of the Cell," 5$^{th}$ edition, Garland Science, New York, N.Y., 2008; Voet, D. et al. "Fundamentals of Biochemistry: Life at the Molecular Level," 3$^{rd}$ edition, John Wiley & Sons, Hoboken, N.J., 2008; Sambrook, J. et al., "Molecular Cloning: A Laboratory Manual," 3$^{rd}$ edition, Cold Spring Harbor Laboratory Press, 2001; Ausubel, F. et al., "Current Protocols in Molecular Biology," John Wiley & Sons, New York, 1987 and periodic updates; Freshney, R. I., "Culture of Animal Cells: A Manual of Basic Technique," 4$^{th}$ edition, John Wiley & Sons, Somerset, N.J., 2000; and the series "Methods in Enzymology," Academic Press, San Diego, Calif.

Marrow Adherent Stem Cells (MSCs)

The present disclosure provides methods for treating TBI and modulating stem cell migration by transplanting SB623 cells to a site of brain injury in a subject. SB623 cells are obtained from marrow adherent stem cells (MSCs), also known as marrow adherent stromal cells and mesenchymal stem cells, by expressing the intracellular domain of the Notch protein in the MSCs. MSCs are obtained by selecting adherent cells (i.e., cells that adhere to tissue culture plastic) from bone marrow.

Exemplary disclosures of MSCs are provided in U.S. patent application publication No. 2003/0003090; Prockop (1997) *Science* 276:71-74 and Jiang (2002) *Nature* 418:41-49. Methods for the isolation and purification of MSCs can be found, for example, in U.S. Pat. No. 5,486,359; Pittenger et al. (1999) *Science* 284:143-147 and Dezawa et al. (2001) *Eur. J. Neurosci.* 14:1771-1776. Human MSCs are commercially available (e.g., BioWhittaker, Walkersville, Md.) or can be obtained from donors by, e.g., bone marrow aspiration, followed by selection for adherent bone marrow cells. See, e.g., WO 2005/100552.

MSCs can also be isolated from umbilical cord blood. See, for example, Campagnoli et al. (2001) *Blood* 98:2396-2402; Erices et al. (2000)*Br. J. Haematol.* 109:235-242 and Hou et al. (2003) *Int. J. Hematol.* 78:256-261. Additional sources of MSCs include, for example, menstrual blood and placenta.

Notch Intracellular Domain

The Notch protein is a transmembrane receptor, found in all metazoans, that influences cell differentiation through intracellular signaling. Contact of the Notch extracellular domain with a Notch ligand (e.g., Delta, Serrate, Jagged) results in two proteolytic cleavages of the Notch protein, the second of which is catalyzed by a γ-secretase and releases the Notch intracellular domain (NICD) into the cytoplasm. In the mouse Notch protein, this cleavage occurs between amino acids gly1743 and val1744. The NICD translocates to the nucleus, where it acts as a transcription factor, recruiting additional transcriptional regulatory proteins (e.g., MAM, histone acetylases) to relieve transcriptional repression of various target genes (e.g., Hes 1).

Additional details and information regarding Notch signaling are found, for example in Artavanis-Tsakonas et al. (1995) *Science* 268:225-232; Mumm and Kopan (2000) *Develop. Biol.* 228:151-165 and Ehebauer et al. (2006) *Sci. STKE* 2006 (364), cm7. [DOI: 10.1126/stke.3642006 cm7].

Cell Culture and Transfection

Standard methods for cell culture are known in the art. See, for example, R. I. Freshney "Culture of Animal Cells: A Manual of Basic Technique," Fifth Edition, Wiley, New York, 2005.

Methods for introduction of exogenous DNA into cells (i.e., transfection), and methods for selection of cells comprising exogenous DNA, are also well-known in the art. See, for example, Sambrook et al. "Molecular Cloning: A Laboratory Manual," Third Edition, Cold Spring Harbor Laboratory Press, 2001; Ausubel et al., "Current Protocols in Molecular Biology," John Wiley & Sons, New York, 1987 and periodic updates.

SB623 Cells

In one embodiment for the preparation of SB623 cells, a culture of MSCs is contacted with a polynucleotide comprising sequences encoding a Notch intracellular domain (NICD); e.g., by transfection; followed by enrichment of transfected cells by drug selection and further culture. See, for example, U.S. Pat. No. 7,682,825 (Mar. 23, 2010); U.S. Patent Application Publication No. 2010/0266554 (Oct. 21, 2010); and WO 2009/023251 (Feb. 19, 2009); all of which disclosures are incorporated by reference, in their entireties, for the purposes of describing isolation of marrow adherent stem cells and conversion of marrow adherent stem cells to SB623 cells (denoted "neural precursor cells" and "neural regenerating cells" in those documents).

In these methods, any polynucleotide encoding a Notch intracellular domain (e.g., vector) can be used, and any method for the selection and enrichment of transfected cells can be used. For example, in certain embodiments, MSCs are transfected with a vector containing sequences encoding a Notch intracellular domain and also containing sequences encoding a drug resistance marker (e.g. resistance to G418). In additional embodiments, two vectors, one containing sequences encoding a Notch intracellular domain and the other containing sequences encoding a drug resistance marker, are used for transfection of MSCs. In these embodiments, selection is achieved, after transfection of a cell culture with the vector or vectors, by adding a selective agent (e.g., G418) to the cell culture in an amount sufficient to kill cells that do not comprise the vector but spare cells that do. Absence of selection entails removal of said selective agent or reduction of its concentration to a level that does not kill cells that do not comprise the vector. Following selection (e.g., for seven days) the selective agent is removed and the cells are further cultured (e.g., for two passages).

Preparation of SB623 cells thus involves transient expression of an exogenous Notch intracellular domain in a MSC. To this end, MSCs can be transfected with a vector comprising sequences encoding a Notch intracellular domain wherein said sequences do not encode a full-length Notch protein. All such sequences are well known and readily available to those of skill in the art. For example, Del Amo et al. (1993) *Genomics* 15:259-264 present the complete amino acid sequences of the mouse Notch protein; while Mumm and Kopan (2000) *Devel. Biol.* 228:151-165 provide the amino acid sequence, from mouse Notch protein, surrounding the so-called S3 cleavage site which releases the intracellular domain. Taken together, these references provide the skilled artisan with each and every peptide containing a Notch intracellular domain that is not the full-length Notch protein; thereby also providing the skilled artisan with every polynucleotide comprising sequences encoding a Notch intracellular domain that does not encode a full-length Notch protein. The foregoing documents (Del Amo and Mumm) are incorporated by reference in their entireties for the purpose of disclosing the amino acid sequence of the full-length Notch protein and the amino acid sequence of the Notch intracellular domain, respectively.

Similar information is available for Notch proteins and nucleic acids from additional species, including rat, *Xenopus, Drosophila* and human. See, for example, Weinmaster et al. (1991) *Development* 113:199-205; Schroeter et al. (1998) *Nature* 393:382-386; NCBI Reference Sequence No. NM_017167 (and references cited therein); SwissProt P46531 (and references cited therein); SwissProt Q01705 (and references cited therein); and GenBank CAB40733 (and references cited therein). The foregoing references are incorporated by reference in their entireties for the purpose of disclosing the amino acid sequence of the full-length Notch protein and the amino acid sequence of the Notch intracellular domain in a number of different species.

In additional embodiments, SB623 cells are prepared by introducing, into MSCs, a nucleic acid comprising sequences encoding a Notch intracellular domain such that the MSCs do not express exogenous Notch extracellular domain. Such can be accomplished, for example, by transfecting MSCs with a vector comprising sequences encoding a Notch intracellular domain wherein said sequences do not encode a full-length Notch protein.

Additional details on the preparation of SB623 cells, and methods for making cells with properties similar to those of SB623 cells which can be used in the methods disclosed herein, are found in U.S. Pat. No. 7,682,825; U.S. Pat. No. 8,133,725; and U.S. Patent Application Publication Nos. 2010/0266554 and 2011/0229442; the disclosures of which are incorporated by reference herein for the purposes of providing additional details on, and alternative methods for the preparation of, SB623 cells, and for providing methods for making cells with properties similar to those of SB623 cells. See also Dezawa et al. (2004) *J. Clin. Invest.* 113: 1701-1710.

Reversal of Symptoms of TBI by Transplantation of SB623 Cells

The efficacy of SB623 cell transplantation as a treatment for TBI was tested in a rat model system. Prior to testing, adult male Sprague-Dawley rats (8-weeks old) were evaluated in motor and neurological tests (all performed by two investigators blinded to the treatment condition throughout the study) to confirm that all animals displayed normal behaviors at baseline (i.e., prior to brain insult). Animals were then exposed to experimental traumatic brain injury (TBI), and seven days later were subjected to the same behavioral tests to confirm the typical TBI-induced motor and neurological impairments. Following these tests (at 7 days post-TBI), the animals were assigned randomly to one of two groups to receive either stereotaxic transplants of Notch-induced bone marrow-derived stem cells (SB623 cells)$^{26,29}$ or vehicle infusion into the cortex (see Example 3).

The inventors have found that, at both one month and three months post-TBI, traumatically injured animals that received transplants of SB623 cells displayed significantly improved motor and neurological functions, coupled with significantly reduced damage to the cortical core and peri-injured cortical areas, compared to traumatically injured animals that received vehicle only (see Examples). These behavioral and physical improvements were achieved with modest graft survival of 0.60% and 0.16% at one month and three months post-TBI, respectively. Other sites in the brain that are affected by TBI include the striatum and the hippocampus; hence transplantation of SB623 cells to the striatum and the hippocampus can also be used for treatment of TBI affecting these areas. In summary, transplantation of SB623 cells into brain-injured animals provided robust functional recovery despite lack of graft persistence.

Creation of a Biobridge by Transplantation of SB623 Cells

Examination of host tissue in brain-injured animals that had received transplants of SB623 cells, at one month post-TBI, revealed a surge of endogenous cell proliferation (detected by Ki67 expression) and differentiation of neurogenic cells (detected by expression of nestin) in the peri-injured cortical areas and subventricular zone (SVZ). A stream of cells (expressing doublecortin) migrating along the corpus callosum (CC) of these animals was also detected. In contrast, animals subjected to experimental TBI that received vehicle alone displayed limited cell proliferation, little neural differentiation, and only scattered migration in the peri-injured cortical areas. In addition, very few newly-formed cells were visible in the sub-ventricular zone of these control animals (see Examples).

At three months post-TBI, the brains from animals that had received SB623 cell transplants exhibited much higher levels of cell proliferation and neural differentiation encasing the peri-injured cortical areas, along with a solid stream of neuronal cells (expressing both nestin and doublecortin) migrating not just along but across the CC from the SVZ to the impacted cortex. Brains from injured animals that had received only vehicle exhibited much more elevated levels of cell proliferation at three months post-TBI than at one month post-TBI, but the newly-formed cells appeared "trapped" within the SVZ and the corpus callosum; with only a small number of cells able to reach the impacted cortex. Quantitative analysis of Ki67, nestin and doublecortin immunoreactivity in the SVZ, the CC, and the injured cortical area indicated that the differences in expression of these markers, between animals receiving SB623 cell transplants and animals receiving only vehicle, were statistically significant.

In a separate experiment, the biobridge formed by endogenous cells migrating from the SVZ to the site of injury was isolated by laser capture microdissection (Espina et al. (2006) *Nature Protoc.* 1:586-603) and its zymogenic properties were analyzed. In this experiment, three groups of animals were analyzed: (1) animals subjected to TBI followed by transplantation of SB623 cells at 7 days post-TBI, (2) animals subjected to TBI followed by infusion of vehicle at 7 days post-TBI, and (3) control sham-operated age-matched adult Sprague-Dawley rats (n=3 per group). Zymographic assays of the laser-captured biobridges from animals subjected to TBI revealed two-fold and nine-fold upregulation of matrix metalloproteinase 9 (MMP-9) expression/activity in animals that received SB623 cell transplants, compared to vehicle-infused animals or sham-operated animals, at one month and three months post-transplantation, respectively (Example 11).

MMPs have been implicated in recovery in chronic brain injury[29], and inhibition of MMP activity has been shown to abrogate migration of neurogenic cells from the SVZ into damaged tissues and to retard neurovascular remodeling[30]. MMPs may thus play a role in facilitating host cell migration towards injured brain areas as part of the process by which SB623 cells provide functional recovery from TBI.

In summary, the inventors have discovered that transplantation of SB623 cells remodeled the traumatically injured brain by creating a biobridge between the SVZ and the peri-injured cortex. This method of cell therapy can now be used to create similar biobridges between neurogenic and non-neurogenic sites, to facilitate injury-specific migration of cells across tissues that might otherwise pose barriers to cell motility.

Formulations, Kits and Routes of Administration

Therapeutic compositions comprising SB623 cells as disclosed herein are also provided. Such compositions typically comprise the SB623 cells and a pharmaceutically acceptable carrier. Supplementary active compounds can also be incorporated into SB623 cell compositions.

The therapeutic compositions disclosed herein are useful for, inter alia, treating TBI and modulating stem cell migration in the brain. Accordingly, a "therapeutically effective amount" of a composition comprising SB623 cells is any amount that reduces symptoms of TBI or that stimulates migration of stem cells in the brain. For example, dosage amounts can vary from about 100; 500; 1,000; 2,500; 5,000; 10,000; 20,000; 50,000; 100,000; 300,000; 500,000; 1,000,000; 5,000,000 to 10,000,000 cells or more (or any integral value therebetween); with a frequency of administration of, e.g., once per day, twice per week, once per week, twice per month, once per month, depending upon, e.g., body weight, route of administration, severity of disease, etc. Thus, a therapeutically effective amount can comprise a plurality of administrations of the same amount, or different amounts, of SB623 cells. In certain embodiments, a single administration of SB623 cells is a therapeutically effective amount.

Various pharmaceutical compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The cells described herein may be suspended in a physiologically compatible carrier for transplantation. As used herein, the term "physiologically compatible carrier" refers to a carrier that is compatible with the SB623 cells and with any other ingredients of the formulation, and is not deleterious to the recipient thereof. Those of skill in the art are familiar with physiologically compatible carriers. Examples of suitable carriers include cell culture medium (e.g., Eagle's minimal essential medium), phosphate buffered saline, Hank's balanced salt solution+/−glucose (HBSS), and multiple electrolyte solutions such as, e.g., Plasma-Lyte™ A (Baxter).

The volume of a SB623 cell suspension administered to a subject will vary depending on the site of transplantation, treatment goal and number of cells in solution. Typically the amount of cells administered will be a therapeutically effective amount. As used herein, a "therapeutically effective amount" or "effective amount" refers to the number of transplanted cells which are required to effect treatment of the particular disorder; i.e., to produce a reduction in the amount and/or severity of the symptoms associated with that disorder. For example, in the case of TBI, transplantation of a therapeutically effective amount of SB623 cells results in reduction and/or reversal of the symptoms of TBI; e.g., restoration of locomotor activity and neurological performance, and stimulation of migration of host neurogenic cells. Therapeutically effective amounts vary with the type and extent of brain damage, and can also vary depending on the overall condition of the subject.

The disclosed therapeutic compositions can also include pharmaceutically acceptable materials, compositions or vehicle, such as a liquid or solid filler, diluent, excipient, solvent or encapsulating material, i.e., carriers. These carriers can, for example, stabilize the SB623 cells and/or facilitate the survival of the SB623 cells in the body. Each carrier should be "acceptable" in the sense of being compatible with the other ingredients of the formulation and not injurious to the subject. Some examples of materials which can serve as pharmaceutically-acceptable carriers include: sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Exemplary formulations include, but are not limited to, those suitable for parenteral administration, e.g., intrapulmonary, intravenous, intra-arterial, intra-ocular, intra-cranial, sub-meningial, or subcutaneous administration, including formulations encapsulated in micelles, liposomes or drug-release capsules (active agents incorporated within a biocompatible coating designed for slow-release); ingestible formulations; formulations for topical use, such as eye drops, creams, ointments and gels; and other formulations such as inhalants, aerosols and sprays. The dosage of the compositions of the disclosure will vary according to the extent and severity of the need for treatment, the activity of the administered composition, the general health of the subject, and other considerations well known to the skilled artisan.

In additional embodiments, the compositions described herein are delivered intracranially at or near a site of traumatic brain injury. Such localized delivery allows for the delivery of the composition non-systemically, thereby reducing the body burden of the composition as compared to systemic delivery. Local delivery can be achieved, for example, by intra-cranial injection, or through the use of various medically implanted devices including, but not limited to, stents and catheters, or can be achieved by inhalation, phlebotomy, or surgery. Methods for coating, implanting, embedding, and otherwise attaching desired agents to medical devices such as stents and catheters are established in the art and contemplated herein.

Another aspect of the present disclosure relates to kits for carrying out the administration of SB623 cells, optionally in combination with another therapeutic agent, to a subject. In one embodiment, a kit comprises a composition of SB623 cells, formulated in a pharmaceutical carrier, suitable for transplantation.

EXAMPLES

In the studies disclosed herein, rats were subjected to experimental traumatic brain injury (TBI) and, seven days later, those having sufficient locomotor and neurological deficits received transplants of either SB623 cells or vehicle to the injured area. Values of locomotor and neurological performance were evaluated prior to TBI (baseline values), again at 7 days after TBI (prior to transplantation), and monthly thereafter for 3 months after TBI.

Following completion of behavioral testing at 1 month and 3 months after TBI, randomly selected animals were euthanized (n=10 per group) by transcardial perfusion with 4% paraformaldehyde. Their brains were removed and sectioned for evaluation of persistence of the transplanted cells, histological appearance of brain tissue in and around the injured area, expression of various neural markers in and around the injured area, and zymogenic activity in and around the injured area.

Transplant outcomes were evaluated using the following criteria: 1) locomotor behavior via elevated body swing test (EBST) and Rotorod; (2) neurological performance via a Bederson-modified neurological examination; 3) lesion volume via histology (H&E stained sections); 4) graft survival via immunohistochemistry using an antibody (HuNu) that specifically detects human cells; and, 5) mechanism-based immunohistochemial analyses of neuroprotection and/or regeneration using antibodies directed against the grafted human cells and host cells.

Example 1: Preparation of MSCs and SB623 Cells

Bone marrow aspirates from adult human donors were obtained from Lonza Walkersville, Inc. (Walkersville, Md.) and plated in α-MEM (Mediatech, Herndon, Va.) supplemented with 10% fetal bovine serum (Hyclone, Logan, Utah), 2 mM L-glutamine (Invitrogen, Carlsbad, Calif.) and penicillin/streptomycin (Invitrogen). Cells were cultured for three days at 37° C. and 5% $CO_2$, to obtain a monolayer of adherent cells. After removal of non-adherent cells, culture was continued under the same conditions for two weeks. During this time, cells were passaged twice, using 0.25% trypsin/EDTA. A portion of the cells from the second passage were frozen as MSCs.

The remaining cells from the second passage were plated and transfected, using Fugene6 (Roche Diagnostics, Indianapolis, Ind.), with a plasmid containing sequences encoding a Notch intracellular domain operatively linked to a cytomegalovirus promoter (pCMV-hNICD1-SV40-Neo$^R$). This plasmid also contained sequences encoding resistance to neomycin and G418 under the transcriptional control of a SV40 promoter. Transfected cells were cultured at 37° C. and 5% $CO_2$ in the growth medium described in the previous paragraph, supplemented with 100 µg/ml G418 (Invitrogen, Carlsbad, Calif.). After seven days, G418-resistant colonies were expanded and the culture was passaged twice. After the second passage, the cells were collected and frozen as SB623 cells.

In an embodiment, preparation of cells for use in inducing proliferation and migration of endogenous neurogenic cells, referred to below as "neural regenerating cells" (NRCs), are prepared by the following method.

Preparation of Marrow Adherent Stromal Cells (MASCs)

Bone marrow aspirates, obtained from human donors, were divided into 12.5 ml aliquots in 50 ml tubes, and 12.5 ml of growth medium (10% FBS in α-MEM, supplemented with penicillin/streptomycin and 2 mM L-glutamine) was added to each tube. The contents of the tubes were mixed by inversion and the tubes were centrifuged at 200×g for 8 minutes. The upper, clear phase was discarded, the volume of the lower phase was adjusted to 25 ml with flesh growth medium, and the tubes were again mixed and centrifuged. The upper layer was again removed. The volume of the lower phase in each tube was again adjusted to 25 ml and the contents of all tubes was pooled in a 250 ml tube. After determination of cell concentration by Trypan Blue exclusion and determination of nucleated cell count, cells were plated in T225 flasks, in 40 ml per flask of growth medium at a density of $100 \times 10^6$ total nucleated cells per flask. The flasks were incubated at 37° C. for 3 days in a $CO_2$ incubator, during which time the MASCs attached to the flask.

After 3 days, unattached cells were removed by rocking the flasks and withdrawing the culture medium. Each flask was washed three times with 40 ml of α-MEM supplemented with penicillin/streptomycin; then 40 ml of prewarmed (37° C.) growth medium was added to each flask and the cells were cultured at 37° C. in a $CO_2$ incubator. During this time, the medium was replaced with 40 ml of fresh growth medium every 3-4 days, and cells were monitored for growth of colonies and cell density.

When the cultures achieved 25-30% confluence (usually 10,000-20,000 cells per colony and within 10-14 days), the MASCs (passage M0) were harvested for further passage.

MASCs were harvested from up to 10 T-225 flasks at a time. Medium was removed from the flasks and the adherent cells were rinsed with 20 ml of DPBS Ca/Mg (DPBS–/–, HyClone) 2 times. Ten ml of 0.25% Trypsin/EDTA (Invitrogen, Carlsbad, Calif.) was added to each flask and flasks were incubated for approximately 5 min at room temperature. When cells had detached and the colonies had dispersed into single cells, the trypsin was inactivated by addition of 10 ml of growth medium followed by gentle mixing. The cell suspensions were withdrawn from the flasks, and pooled in 250 ml tubes. The tubes were subjected to centrifugation at 200×g for 8 minutes. The supernatants were carefully removed and the wet cell pellets were resuspended in growth medium to an estimated cell concentration of approximately $1 \times 10^6$ cells/ml. Viable cell count was determined and cells were plated in T225 flasks at a concentration of $2 \times 10^6$ cells per flask in growth medium (passage M1). Cells were grown for 3-5 days, or until 85-90% confluent, changing medium every 2 to 3 days. At 85-90% confluence, passage M1 cells were harvested by trypsinization and replated at $2 \times 10^6$ cells per T225 flask as described above, to generate passage M2 cultures. M2 cultures were fed fresh medium every three days, if necessary. When passage M2 cultures reached 85-90% confluence (usually within 3-5 days), they were either harvested for transfection to generate NRCs (see below) or frozen for future use.

Preparation of Neural Regenerating Cells (NRCs)

Neural regenerating cells were made by transfection of passage M2 MASCs with a plasmid encoding the Notch intracellular domain. The plasmid (pCI-Notch) comprised a pCI-neo backbone (Promega, Madison, Wis.) in which sequences encoding amino acids 1703-2504 of the human Notch-1 protein, which encode the intracellular domain, were introduced into the multiple cloning site. For each flask of MASCs, 5 ml of transfection mixture, containing 40 μg of plasmid and 0.2 ml of Fugene 6® solution, was used. To make the transfection mixture, the appropriate amount of Fugene® solution (depending on the number of flasks of cells to be transfected) was added to α-MEM in a sterile 250 ml tube, using a glass pipette. The solution was mixed gently and incubated for 5 min at room temperature. The appropriate amount of plasmid DNA was then added dropwise to the Fugene®/α-MEM mixture, gently mixed, and incubated for 30 mm at room temperature.

Prior to the addition of pCI-Notch DNA to the Fugene®/MEM mixture, 5 ml was removed and placed into a 15 ml tube to which was added 40 ug of pEGFP plasmid. This solution was used to transfect one flask of cells_ as a control for transfection efficiency.

For transfection, passage M2 MASCs were harvested by trypsinization (as described above) and plated at a density of $2.5 \times 10^6$ cells in 40 ml of growth medium per T225 flask. When the cells reached 50-70% confluence (usually within 18-24 hours) they were prepared for transfection, by replacing their growth medium with 35 ml per flask of transfection medium (α-MEM+10% FBS without penicillin/streptomycin).

Three hours after introduction of transfection medium, 5 ml of the transfection mixture (see above) was added to each T-225 flask by pipetting directly into the medium, without contacting the growth surface, followed by gentle mixing. A control T-225 flask was transfected with 40 μg of pEGFP plasmid, for determination of transfection efficiency.

After incubating cultures at 37° C. in transfection medium for 24 hours, the transfection medium was replaced with α-MEM+10% FBS+penicillin/streptomycin.

Cells that had incorporated plasmid DNA were selected 48 hrs after transfection by replacing the medium with 40 ml per flask of selection medium (growth medium containing 100 μg/ml G-418). Fresh selection medium was provided 3 days, and again 5 days after selection was begun. After 7 days, selection medium was removed and the cells were fed with 40 ml of growth medium. The cultures were then grown for about 3 weeks (range 18 to 21 days), being re-fed with fresh growth medium every 2-3 days.

Approximately 3 weeks after selection was begun, when surviving cells began to form colonies, cells were harvested. Medium was removed from the flasks using an aspirating pipette and 20 ml of DPBS without $Ca^{2+}/Mg^{2+}$, at room temperature, was added to each flask. The cults re surface was gently rinsed, the wash solution was removed by aspiration and the rinse step was repeated. Then 10 ml of prewarmed (37° C.) 0.25% Trypsin/EDTA was added to each flask, rinsed over the growth surface, and the flasks were incubated for 5-10 min. at room temperature. Cultures were monitored with a microscope to ensure complete detachment of cells. When detachment was complete, trypsin was inactivated by addition of 10 ml of growth medium per flask. The mixture was rinsed over the culture surface, mixed by pipetting 4-5 times with a 10 ml pipette, and the suspension was transferred into a sterile 50 ml conical centrifuge tube. Cells harvested from several flasks could be pooled in a single tube. If any clumps were present, they were allowed to settle and the suspension was removed to a fresh tube.

The cell suspensions were centrifuged at 200×g for 8 min at room temperature. Supernatants were removed by aspiration. Cell pellets were loosened by tapping the tube, about 10 ml of DPBS without. $Ca^{2+}/Mg^{2+}$ was added to each tube and cells were resuspended by gently pipetting 4-5 times with a 10 ml pipette to obtain a uniform suspension.

For expansion of transfected cells, cell number was determined for the suspension of transformed, selected cells and the cells were plated in T-225 flasks at $2 \times 10^6$ cells per flask (providing approximately 30% seeding of viable cells). This culture is denoted M2P1 (passage #1). M2P1 cultures were fed with fresh medium every 2-3 days, and when cells reached 90-95% confluence (usually 4-7 days after passage), they were harvested and replated at $2 \times 10^6$ cells per flask to generate passage M2P2. When M2P2 cultures reached 90-95% confluence, they were harvested for cryopreservation or for further assay.

Cryopreservation

MASCs and NRCs were frozen for storage according to the following procedure. MASCs were typically frozen after passage M2, and NRCs were typically frozen after passage M2P2. Processing 4-5 flasks at a time, medium was aspirated from the culture flasks, 10 ml of 0.25% Trypsin/EDTA (at room temperature) was added to each flask, gently rinsed over the culture surface for no longer than 30 sec, and removed by aspirating. Then 10 ml of warmed (37° C.) 0.25% Trypsin/EDTA was added to each flask, rinsed over the growth surface, and the flasks were incubated for 5-10 min. at room temperature. Cultures were monitored by microscopic examination to ensure complete detachment of cells.

When detachment was complete, 10 ml of α-MEM growth medium was added to each flask, rinsed over the culture surface, and detached cells were mixed by pipetting 4-5 times with a 10 ml pipette. The cell suspension was transferred into a sterile 250 ml conical centrifuge tube, and any large clumps of cells were removed. Cells harvested from 15-20 flasks were pooled into one 250 ml tube.

The tube was subjected to centrifugation at 200×g for 8 min at room temperature. The supernatant was removed by aspirating. The pellet was loosened by tapping the tube, and about 25 ml of DPBS (−/−) was added to each tube. Cells were resuspended by gently pipetting 4-5 times with a 10 ml pipette to obtain a uniform suspension. Any clumps in the suspension were removed by pipetting each sample through a sterile 70 μm sieve placed in the neck of a 50 ml tube.

Cell suspensions were pooled in a 250 ml centrifuge tube and any remaining clumps were removed. The final volume was adjusted to 200 ml with DPBS (−/−) and the sample was subjected to centrifugation at 200×g for 8 min at room temperature. The supernatant was removed by aspiration. The cell pellet was loosened by tapping, 20 ml of DPBS (−/−) was added to the tube and cells were resuspended by mixing well and gently pipetting with a 10 ml pipette. The final volume was adjusted with DPBS (−/−) to give an estimated concentration of approximately $0.5$-$1.0 \times 10^6$ cells/ml, usually about 4-5 ml per T225 flask harvested, or about 200 ml for a 40-flask harvest. A viable cell count was conducted on the suspension, which was then subjected to centrifugation at 200×g for 8 minutes. The supernatant was aspirated, and the cell pellet was resuspended in cold Cryo Stor solution (BioLife Solutions, Bothell, Wash.) to a concentration of $12 \times 10^6$ cells/ml. One ml aliquots were dispensed into vials, which were sealed and placed at 4° C. in a Cryo Cooler. Vials were transferred into a CryoMed (Thermo Forma) freezer rack and frozen.

MSCs and SB623 cells prepared as described herein were thawed as required and used for further study.

Example 2: Induction of TBI in a Rat Model

A total of 40 animals identified at baseline (prior to TBI surgery) as exhibiting normal behaviors (50-60% bias swing activity in EBST; 60 seconds staying time on Rotorod; and a mean Bederson score of at most 0-0.5), received TBI surgery as described below.

All surgical procedures were conducted under aseptic conditions. Adult male Sprague-Dawley rats were anesthetized with 1.5% isofluorane and checked for pain reflexes. Under deep anesthesia, animals underwent a moderate TBI model, as follows. Each animal was placed in a stereotaxic frame, with anesthesia being maintained with 1-2% isofluorane administered via a gas mask. After exposing the skull, a 4-mm craniectomy was performed over the left frontoparietal cortex, with its center at −2.0 mm AP and +2.0 mm ML to the bregma. A pneumatically operated metal impactor, with a diameter of 3 mm, was used to impact the brain at a velocity of 6.0 m/s, reaching a depth of 1.0 mm below the dura mater layer and remaining in the brain for 150 milliseconds. The impactor rod was angled 15° to the vertical, so as to be perpendicular to the tangential plane of the brain surface at the impact site. A linear variable displacement transducer (Macrosensors, Pennsauken, N.J.) connected to the impactor was used to measure velocity and duration, to verify consistency.

Subsequent to controlled cortical impact injury, the incision was sutured after bleeding ceased. An integrated heating pad and rectal thermometer unit with feedback control allowed maintenance of body temperature at normal limits. All animals were monitored until recovery from anesthesia. In addition, animals were weighed and observed daily for three consecutive days following induction of TBI, weighed twice a week thereafter, and monitored daily throughout the study for health status and any signs that indicated problems or complications.

Example 3: Grafting of SB623 Cells

Of the animals subjected to TBI, only those having the following degree of behavioral impairment at Day 7 post-TBI were selected for transplantation studies: at least 75% bias swing activity in the EBST; 30 seconds or less staying time on the Rotorod; and a mean Bederson score of at least 2.5. Those animals that were selected were randomly assigned either to a group receiving SB623 transplants (n=20) or to a group receiving vehicle infusion (n=20). The target area for transplantation was the medial cortex, which corresponded to the peri-injured cortical area based on previously established target sites for similar stereotaxic implants.

All surgical procedures were conducted under aseptic conditions. Animals were anesthetized with 1.5% isofluorane and checked for pain reflexes. Once deep anesthesia was achieved (as determined by the loss of pain reflex), the hair was shaved around the area of the surgical incision (skull area), leaving enough border to prevent contamination of the operative site. This was followed by two surgical germicidal scrubs of the site, and draping with sterile drapes.

The animal was then fixed to a stereotaxic apparatus (Kopf Instruments, Tujunga, Calif.), and a small opening was made in the skull with a burr. The coordinates of the opening were 0.5 mm anterior and 1.0 mm lateral to the bregma and 2.0 mm below the dural surface; these were selected to correspond to the cortical area adjacent to the core injury site, based on the atlas of Paxinos and Watson (1998). A 26-gauge Hamilton syringe, containing test material, was then lowered into the opening. With a single needle pass, 3 deposits of 3 ul each were made. Each deposit consisted of 100,000 viable cells in 3 ul of Plasmalyte A, infused over a period of 3 minutes. Following an additional 2-minute absorption time, the needle was retracted and the wound was closed with a stainless steel wound clip. A heating pad and a rectal thermometer allowed maintenance of body temperature at about 37° C. throughout surgery and following recovery from anesthesia. Control injections contained Plasmalyte A only.

Treated and control animals were subjected to elevated body swing test (EBST, Example 4), neurological examination (Example 5), and the Rotorod test (Example 6) at baseline (prior to TBI), at 7 days after TBI (just prior to transplantation) and monthly thereafter up to 3 months post-TBI.

In addition, brains of treated and control animals were characterized histologically at one and three months post-TBI to determine degree of damage (Examples 8 and 9); the extent of proliferation, migration and neural differentiation of host cells (Example 10); and the presence of zymogenic activity (Example 11).

Example 4: Elevated Body Swing Test (EBST)

All investigators testing the animals were blinded to the treatment condition. The EBST was conducted by handling the animal by its tail and recording the direction in which the animal swung its head. The test apparatus consisted of a clear Plexiglas box (40×40×35.5 cm). The animal was gently picked up at the base of the tail, and elevated by the tail until the animal's nose was at a height of 2 inches (5 cm) above the surface. The direction of the swing (left or right) was recorded once the animal's head moved sideways approximately 10 degrees from the midline position of the body. After a single swing, the animal was placed back in the Plexiglas box and allowed to move freely for 30 seconds prior to retesting. These steps were repeated for a total of 20 assays for each animal. Uninjured rats display a 50% swing bias, that is, the same number of swings to the left and to the right. A 75% swing bias indicated 15 swings in one direction and 5 in the other during 20 trials. Previous results utilizing the EBST have indicated that unilaterally lesioned animals display >75% biased swing activity at one month after a nigrostriatal lesion or unilateral hemispheric injury; and that such asymmetry is stable for up to six months[3,26].

Figure 1:
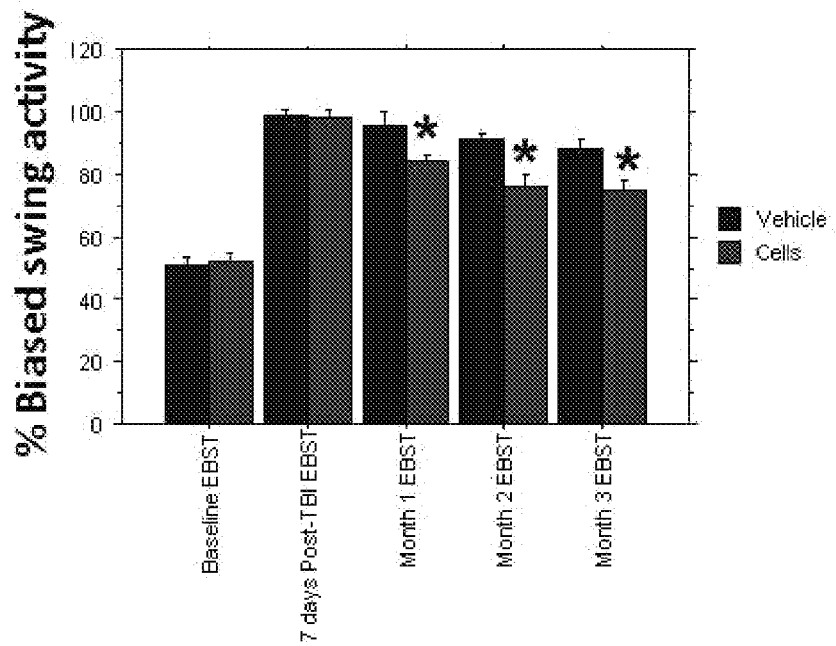
FIG. 1 shows results of the elevated body swing test (EBST) in rats. Values are provided for Baseline (before TBI) and for 7 days, 1 month, 2 months and 3 months after TBI. The rats received either transplants of SB623 cells ("Cells," right-most bar in each pair) or infusion of vehicle ("Vehicle," left-most bar in each pair). "*" indicates statistical significance with a $p<0.05$.

The results of the EBST are shown in FIG. 1. After TBI, essentially all animals exhibited biased swing activity. In animals transplanted with SB623 cells, biased swing activity steadily decreased over the three-month period following TBI and transplantation. By contrast, in animals transplanted with vehicle, the percentage of animals exhibiting biased swing activity after TBI remained essentially unchanged.

Example 5: Modified Bederson Neurological Examination

About one hour after conclusion of the EBST, a modified Bederson-Neurological exam was conducted, following the procedures previously described[3,26] with minor modifications. Neurologic score for each rat was obtained using 3 tests which included (1) forelimb retraction, which measured the ability of the animal to replace the forelimb after it was displaced laterally by 2 to 3 cm, graded from 0 (immediate replacement) to 3 (replacement after several seconds or no replacement); (2) beam walking ability, graded 0 for a rat that readily traversed a 2.4-cm-wide, 80-cm-long beam to 3 for a rat unable to stay on the beam for 10 seconds; and (3) bilateral forepaw grasp, which measured the ability to hold onto a 2-mm-diameter steel rod, graded 0 for a rat with normal forepaw grasping behavior to 3 for a rat unable to grasp with the forepaws. The scores from all 3 tests, which were conducted over a period of about 15 minutes on each assessment day, were added to give a mean neurologic deficit score (maximum possible score, 9 points divided by 3 tests=3).

Figure 2:
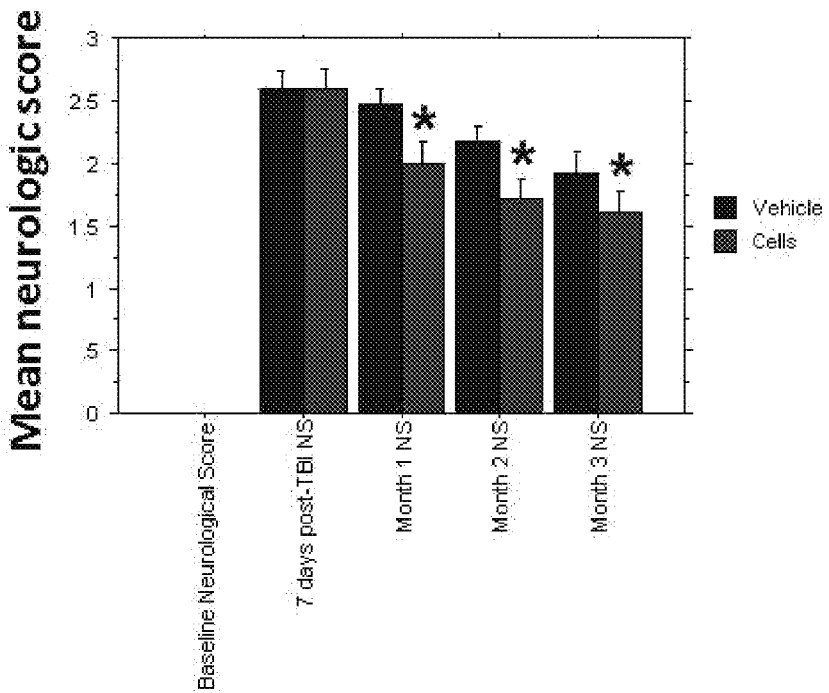
FIG. 2 shows mean scores in a modified Bederson neurological examination in rats subjected to TBI that subsequently received either transplants of SB623 cells ("Cells") or infusion of vehicle ("Vehicle"). Values are provided for Baseline (before TBI) and for 7 days, 1 month, 2 months and 3 months after TBI. The left-most bar in each pair represents the score in rats infused with vehicle; the right-most bar in each pair represents the score in rats that received transplants of SB623 cells. "*" indicates statistical significance with a $p<0.05$.

The results of these neurological examinations are shown in FIG. 2. After TBI, the mean neurological score was 2.5 (out of 3) in all animals. In animals transplanted with SB623 cells, this score was steadily reduced (indicating improved neurological function) over the three-month period following TBI and transplantation. Improvement of neurological function in animals transplanted with SB623 cells was statistically significant ($p<0.05$) compared to animals that had been infused with vehicle.

Example 6: Rotorod® Test

One hour after completion of the neurological exam, the animals were subjected to the Rotorod® test. This test involved placement of the animal on a rotating treadmill that accelerates from 4 rpm to 40 rpm over a 60-second period (Rotorod®, Accuscan, Inc., Columbus, Ohio). The total number of seconds an animal was able to remain on the treadmill was recorded and used as an index of motor coordination. Previous results using a TBI model system have shown that injured animals were able to remain on the Rotorod for significantly shorter times, compared to sham-operated or normal controls.

Figure 3:
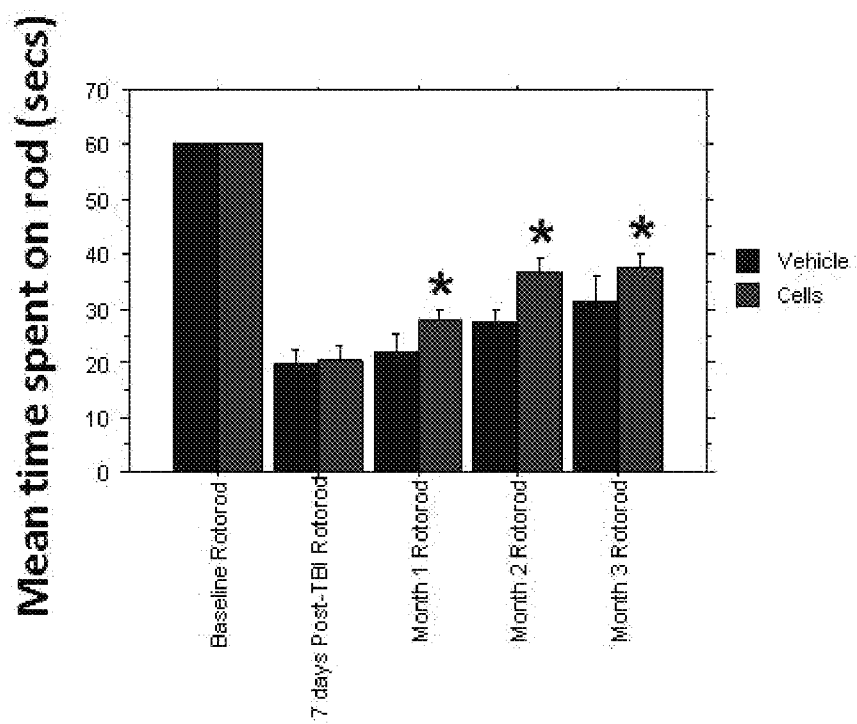
FIG. 3 shows mean values for the number of seconds rats were able to remain on a Rotorod apparatus. The rats were subjected to experimental TBI and subsequently received either transplants of SB623 cells ("Cells") or infusion of vehicle ("Vehicle"). Values are provided for Baseline (before TBI) and for 7 days, 1 month, 2 months and 3 months after TBI. The left-most bar in each pair represents the score in rats infused with vehicle; the right-most bar in each pair represents the score in rats that received transplants of SB623 cells. "*" indicates statistical significance with a $p<0.05$.

The results of this assay are shown in FIG. 3. Uninjured animals were able to remain on the treadmill for an average of 60 seconds. The mean time on the treadmill fell to below 20 seconds seven days after TBI. In animals transplanted with SB623 cells after TBI, mean time on the treadmill doubled to approximately 40 seconds. These improvements were statistically significant compared to animals subjected to TBI that had been infused with vehicle.

Example 7: Perfusion and Sectioning

At 1 month and 3 months after TBI, following completion of behavioral testing as described in Examples 4-6, randomly-selected rats were euthanized (n=10 per group) by transcardial perfusion with 4% paraformaldehyde. The brains were dissected, post-fixed overnight in 4% paraformaldehyde, then immersed in 30% sucrose. Beginning at bregma-5.2 mm anteriorly, each forebrain was cut into 40 um coronal sections, moving posteriorly until bregma-8.8 mm. Sections were processed for determinations of brain damage and analysis of cell survival in the peri-lesion area as described in Examples 8 and 9.

Example 8: Measurement of Brain Damage

Preparation and examination of brain sections was undertaken to identify the extent of brain damage and host cell survival. At least 4 coronal tissue sections per brain were processed for hematoxylin and eosin (H&E) or Nissl staining Cerebral damage was quantitated by determining the indirect lesion area, which was calculated by subtracting the intact area of the ipsilateral hemisphere from the area of the contralateral hemisphere. The lesion volume was presented as a volume percentage of the lesion compared to the contralateral hemisphere, by summing lesion areas from serial sections.

Figure 4:
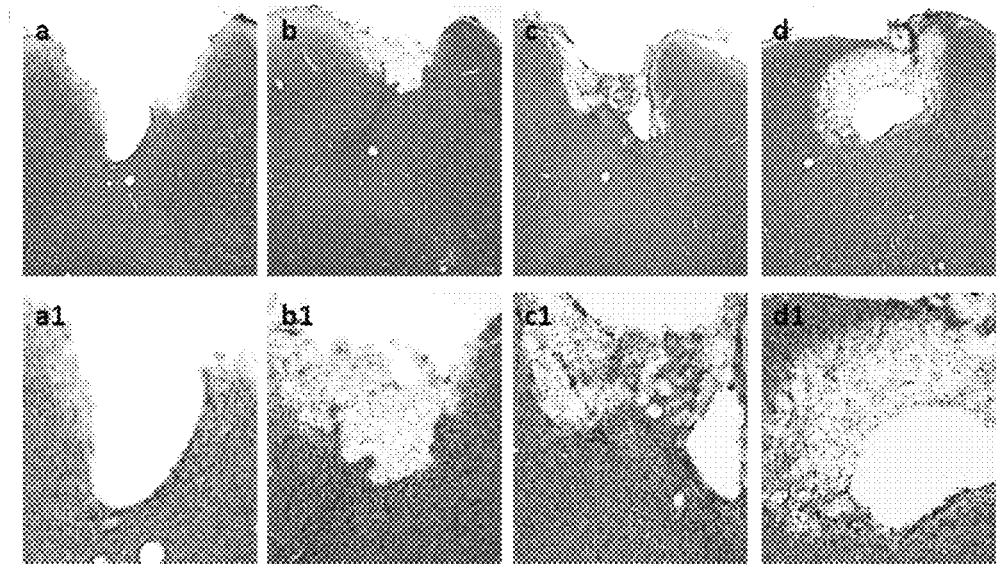
FIGS. 4A and 4B shows results of assays for damage to the cortical core ("Core") and to the cortical region in and around the impact site ("Peri-injury") in rats subjected to TBI.
Figure 4:
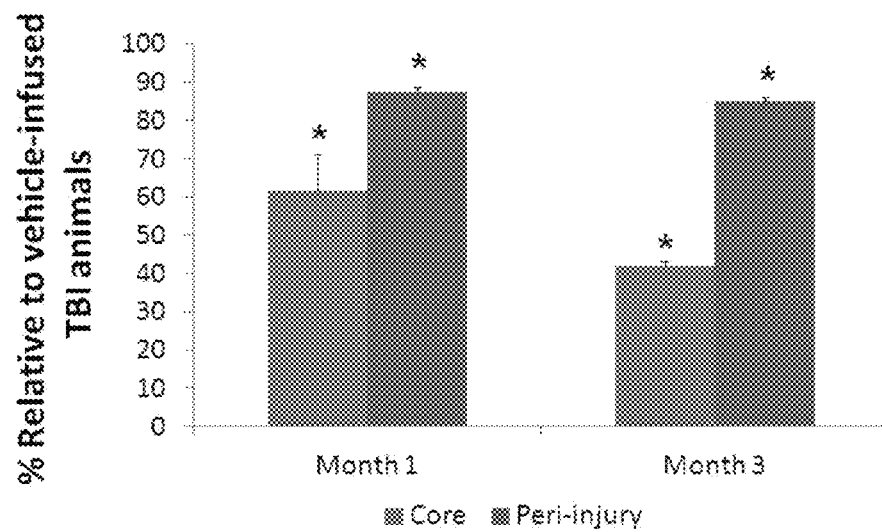

The results, shown quantitatively in FIG. 4B, indicate that animals subjected to TBI that received transplants of SB623 cells experienced significantly less damage to the cortical core and the peri-injured cortical areas, compared to animals subjected to TBI that received infusion of vehicle.

Example 9: Analysis of Cell Survival in the Peri-TBI Lesion Area

Randomly selected high power fields, corresponding to the peri-injured cortical area, were examined to count surviving host cells in this region. Results are shown in FIG. 4A.

Example 10: Immunohistochemistry

Floating sections were processed for immunofluorescent microscopy. Briefly, 40 µm cryostat sectioned tissues were examined at 4× magnification and digitized using a PC-based Image Tools computer program. Engraftment of transplanted SB623 cells was assessed using monoclonal human specific antibody HuNu that did not cross-react with rodent proteins. Additional brain sections were processed for mechanism-based immunohistochemical analyses of brain tissue samples focusing on cell proliferation (Ki67), migration (doublecortin or DCX) and neural differentiation (nestin). Brain sections were blind-coded and Abercrombie's formula was used to calculate the total number of immuno-positive cells[3,26].

Figure 5:
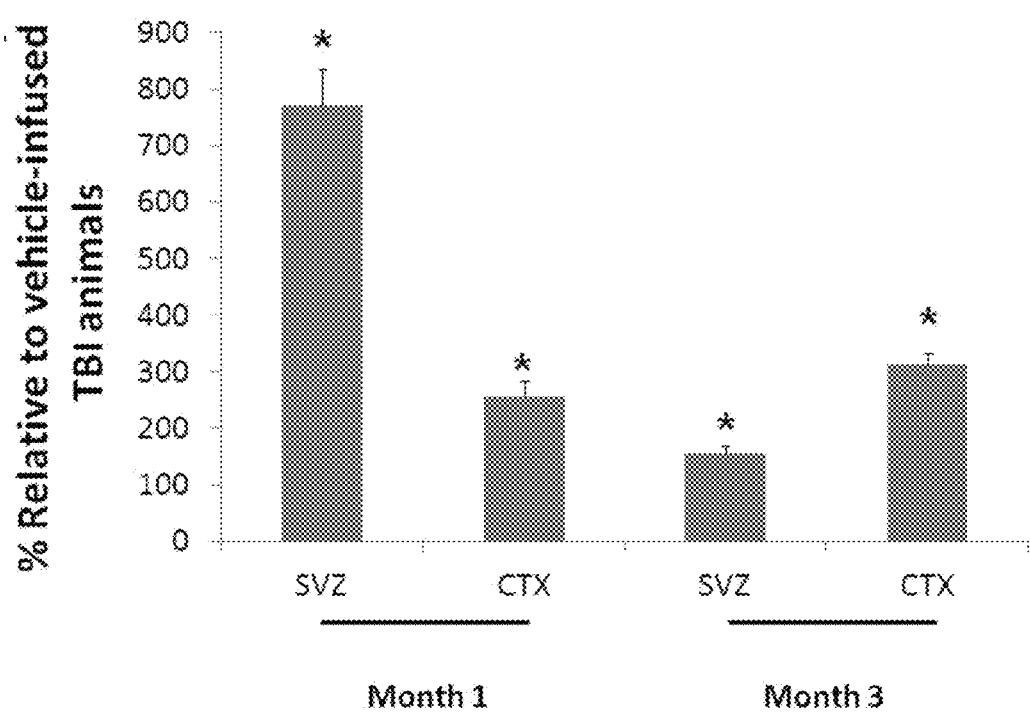
FIG. 5 shows levels of Ki67-labeled cells in the subventricular zone ("SVZ") and the cortex ("CTX") of animals subjected to TBI that received transplants of SB623 cells, compared to animals subjected to TBI that received infusions of vehicle, at one month and three months after TBI. "*" indicates a statistically significant increase in the number of labeled cell observed per high-power field ($p<0.05$).
Figure 6:
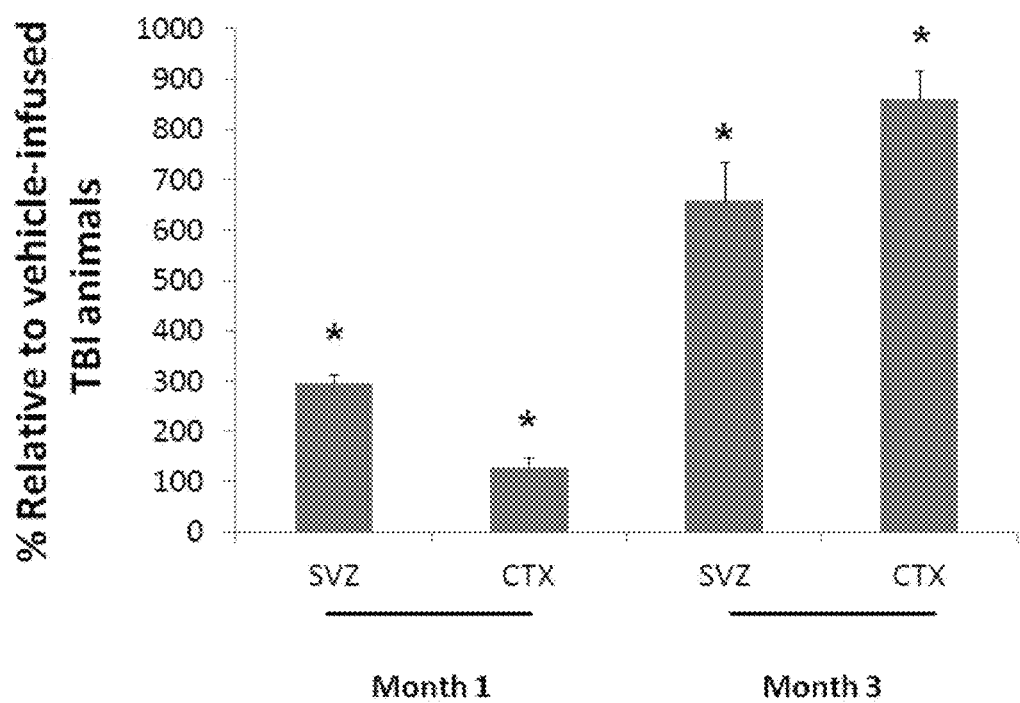
FIG. 6 shows levels of nestin-labeled cells in the subventricular zone ("SVZ") and the cortex ("CTX") of animals subjected to TBI that received transplants of SB623 cells, compared to animals subjected to TBI that received infusions of vehicle, at one month and three months after TBI.

The results of these analyses showed that transplantation of SB623 cells induced formation of a biobridge between the SVZ and the impacted cortex consisting of highly proliferative, neurally committed and migratory cells. At one month post-TBI, immunofluorescent and confocal microscopy revealed a surge of endogenous cell proliferation (evidenced by cells expressing Ki67) and immature neural differentiation (cells expressing nestin) in the peri-injured cortical areas and subventricular zone (SVZ), with a stream of migrating cells (cells expressing doublecortin) along the corpus callosum (CC) of the animals that had received transplants of SB623 cells. Brains from animals that had received vehicle alone displayed limited cell proliferation and neural differentiation, and scattered migration in the peri-injured cortical areas, with almost no newly formed cells present in the SVZ. At three months post-TBI, the brains from SB623-transplanted animals exhibited much more massive cell proliferation and neural differentiation encasing the peri-injured cortical areas, accompanied by a solid stream of neuronally labeled cells (expressing both nestin and doublecortin) migrating, not just along, but across the CC from the SVZ to the impacted cortex. By contrast, in brains from vehicle-infused animals, cell proliferation was enhanced, but the newly formed cells were "trapped" within the SVZ and the CC and only a few cells were able to reach the impacted cortex. Quantitative analyses of Ki67, nestin and DCX immunolabeled cells in SVZ, CC and CTX revealed statistically significant differences between transplanted and vehicle-infused animals (FIGS. 5-7).

Example 11: Zymography

A separate cohort of animals from that whose analysis was described in Examples 4-10 was used to test for the presence and/or activity of proteolytic enzymes after transplantation of SB623 cells into injured brain. Rats were subjected to TBI, then transplanted with either SB623 cells or vehicle. A control group of age-matched sham-operated adult Sprague-Dawley rats was subjected to the same experimental procedure (n=3 rats per group). At one month and three months after TBI, tissue corresponding to the biobridge formed by the cells migrating from the SVZ to the impacted cortex was obtained by laser dissection. After extraction, the tissue was placed in cryotubes and flash frozen in liquid nitrogen. The tubes were stored in a −80° C. freezer until homogenization.

Samples were homogenized in 450 μL of cold working buffer containing 50 mM Tris-HCl (pH 7.5), 75 mM NaCl, and 1 mM PMSF. The tissue was processed with a homogenizer for 10 minutes and centrifuged at 4° C. for 20 minutes at 13000 rpm. The supernatants were separated, frozen and kept at −80° C. until use. The total protein concentration in the supernatant was assessed by the Bradford method.

On the day that zymography was conducted, a volume equivalent to 50 μg of total protein was loaded into a freshly prepared gelatin zymography gel. All gels contained a control lane that was loaded with 0.5 ng recombinant MMP-9, which was used as a standard for both enzyme amount (in ng) and gelatinolytic activity (expressed as relative optical density units, see below). Proteins were electrophoretically separated in the gel under non-reducing conditions at 100 V. After electrophoresis the gels were washed in 125 ml 2.5% Triton twice for 20 minutes. The gels were then incubated in activation buffer (Zymogram Development Buffer, Bio-Rad, Hercules, Calif.) for 20 hours at 37° C. The next day, the gels were stained with Coomassie Blue R-250 Staining Solution (Bio-Rad) for 3 hours and destained for 25 minutes with Destain Solution (Bio-Rad). The gelatinolytic activity of the samples was assessed by densitometric analysis (Gel-Pro v 3.1, Media Cybernetics, Carlsbad, Calif.) of the bands. The molecular weights of proteins in regions of the gel exhibiting lytic activity were determined by comparison to pre-stained standard protein marker (Bio-Rad) run on the same gel. Activity was expressed as optical density relative to that of 0.5 ng of recombinant MMP-9, which was run in the gel as a standard.

The results are shown in FIG. 8. The laser-captured biobridges (corresponding to brain tissue between the SVZ and the impacted cortex) from animals transplanted with SB623 cells after TBI expressed high levels of MMP-9 gelatinolytic activity at one month and three months post-TBI. The levels in SB623-treated animals were significantly higher than those in biobridges from vehicle-infused and sham-operated animals (p<0.05) at both time points. Although biobridges from vehicle-infused animals showed a significant increase in MMP-9 activity compared to sham-operated animals at one month post-TBI, these levels reverted to control levels (i.e., not significantly different from those of sham-operated animals) at three months post-TBI.

For detection on blots, membranes were blocked with blotting grade non-fat dry milk (Bio-Rad). After washing with 0.1% tween 20-tris-buffered saline (TTBS), the membranes were incubated with 1 ug/ml anti MMP-9 monoclonal mouse antibody overnight at 4° C. Membranes were washed again in TTBS, incubated with secondary antibody (1:1,000 dilution of horseradish peroxidase-conjugated goat anti-mouse IgG, Calbiochem) for one hour and finally developed with horseradish peroxidase development solution (ECL advance detection kit, Amersham). The membranes were exposed to autoradiography films (Hyblot CL, Denville Scientific Inc.). The density of the sample bands for the zymograms was expressed as maximal optical density relative to the standard band (0.5 ng recombinant MMP-9).

REFERENCES

1. Joyner, A. L. et al. Production of a mutation in mouse En-2 gene by homologous recombination in embryonic stem cells. *Nature* 338, 153-156 (1989)
2. Yasuhara, T. et al. Transplantation of human neural stem cells exerts neuroprotection in a rat model of Parkinson's disease. *J. Neurosci.* 26, 12497-12511 (2006)
3. Yasuhara, T. et al. Intravenous grafts recapitulate the neurorestoration afforded by intracerebrally delivered multipotent adult progenitor cells in neonatal hypoxic-ischemic rats. *J. Cereb. Blood Flow Metab.* 28, 1804-1810 (2008)
4. Borlongan, C. V. et al. Central nervous system entry of peripherally injected umbilical cord blood cells is not required for neuroprotection in stroke. *Stroke* 35, 2385-2389 (2004)
5. Pastori, C. et al. Arterially perfused neurosphere-derived cells distribute outside the ischemic core in a model of transient focal ischemia and reperfusion in vitro. *PLoS One* 3, e2754 (2008)
6. Redmond, D. E. Jr. et al. Behavioral improvement in a primate Parkinson's model is associated with multiple homeostatic effects of human neural stem cells. *Proc. Natl. Acad. Sci. U.S.A.* 104, 12175-12180 (2007)
7. Lee, J. P. et al. Stem cells act through multiple mechanisms to benefit mice with neurodegenerative metabolic disease. *Nat. Med.* 13, 439-447 (2007)
8. Ma, D. K. et al. Epigenetic choreographers of neurogenesis in the adult mammalian brain. *Nat. Neurosci.* 13, 1338-1344 (2010)

9. Hong, S. H. et al. Cell fate potential of human pluripotent stem cells is encoded by histone modifications. *Cell Stem Cell.* 9, 24-36 (2011)
10. Kim, Y. et al. Mouse B-type lamins are required for proper organogenesis but not by embryonic stem cells. *Science.* 334, 1706-1710 (2011)
11. Borlongan, C. V. Bone marrow stem cell mobilization in stroke: a 'bonehead' may be good after all! *Leukemia* 25, 1674-1686 (2011)
12. Barha, C. K. et al. Progesterone treatment normalizes the levels of cell proliferation and cell death in the dentate gyms of the hippocampus after traumatic brain injury. *Exp. Neurol.* 231, 72-81 (2011)
13. Jaskelioff, M. et al. Telomerase reactivation reverses tissue degeneration in aged telomerase-deficient mice. *Nature* 469, 102-106 (2011)
14. Wang, L. et al. Tumor necrosis factor α primes cerebral endothelial cells for erythropoietin-induced angiogenesis. *J. Cereb. Blood Flow Metab.* 31, 640-647 (2011)
15. Andres, R. H. et al. Human neural stem cells enhance structural plasticity and axonal transport in the ischaemic brain. *Brain.* 134, 1777-1789 (2011)
16. Liu, Z. et al. Bone marrow stromal cells promote skilled motor recovery and enhance contralesional axonal connections after ischemic stroke in adult mice. *Stroke* 42, 740-744 (2011)
17. Mazzocchi-Jones, D. et al. Embryonic striatal grafts restore bi-directional synaptic plasticity in a rodent model of Huntington's disease. *Eur. J. Neurosci.* 30, 2134-2142 (2009)
18. Lee, H. S. et al. Foxa2 and Nurr1 synergistically yield A9 nigral dopamine neurons exhibiting improved differentiation, function, and cell survival. *Stem Cells* 28, 501-512 (2010)
19. Hargus, G. et al. Differentiated Parkinson patient-derived induced pluripotent stem cells grow in the adult rodent brain and reduce motor asymmetry in Parkinsonian rats. *Proc. Natl. Acad. Sci. U.S.A.* 107, 15921-15926 (2010)
20. Yasuda, A. et al. Significance of remyelination by neural stem/progenitor cells transplanted into the injured spinal cord. *Stem Cells.* 29, 1983-1994 (2011)
21. Mezey, E. The therapeutic potential of bone marrow-derived stem cells. *J. Cell. Biochem.* 112, 2683-2687 (2011)
22. Sanai, N. et al. Corridors of migrating neurons in the human brain and their decline during infancy. *Nature* 478, 382-386 (2011)
23. Carlén, M. et al. Forebrain ependymal cells are Notch-dependent and generate neuroblasts and astrocytes after stroke. *Nat. Neurosci.* 12, 259-267 (2009)
24. Robel, S. et al. The stem cell potential of glia: lessons from reactive gliosis. *Nat. Rev. Neurosci.* 12, 88-104 (2011)
25. Seol, H. J. et al. Genetically engineered human neural stem cells with rabbit carboxyl esterase can target brain metastasis from breast cancer. *Cancer Lett.* 311, 152-159 (2011)
26. Yasuhara, T. et al. Notch-induced rat and human bone marrow stromal cell grafts reduce ischemic cell loss and ameliorate behavioral deficits in chronic stroke animals. *Stem Cells Dev.* 18, 1501-1514 (2009)
27. Pollock, K. et al. A conditionally immortal clonal stem cell line form human cortical neuroepithelium for the treatment of ischemic stroke. *Exp. Neurol.* 199, 143-155 (2006)
28. Dezawa, M. et al. Specific induction of neuronal cells from bone marrow stromal cells and application for autologous transplantation. *J Clin Invest.* 113, 1701-10 (2004)
29. Zhao, B. Q., Tejima, E., Lo, E. H. Neurovascular proteases in brain injury, hemorrhage and remodeling after stroke. *Stroke.* 38, 748-752 (2007)
30. Zhao, B. Q. et al. Role of matrix metalloproteinases in delayed cortical responses after stroke. *Nat. Med.* 12, 441-445 (2006)

What is claimed is:

1. A process wherein:
   (a) exogenous cells are implanted at or near an area of brain injury in a subject;
   (b) the implanted exogenous cells produce a biological bridge;
   (c) the implanted exogenous cells do not persist; and
   (d) implantation of the exogenous cells induces migration of endogenous neurogenic cells, along the biological bridge, from a neurogenic niche to the area of brain injury;
   wherein the exogenous cells are obtained by a process comprising:
      (i) providing a culture of MSCs,
      (ii) contacting the cell culture of step (i) with a polynucleotide comprising sequences encoding a Notch intracellular domain (NICD) wherein said polynucleotide does not encode a full-length Notch protein,
      (iii) selecting cells that comprise the polynucleotide of step (ii), and
      (iv) further culturing the selected cells of step (iii) in adherent culture in the absence of selection.

2. The process of claim 1, wherein the brain injury is a traumatic brain injury.

3. The process of claim 2, wherein the traumatic brain injury results from external mechanical force.

4. The process of claim 1, wherein the subject is a human.

5. The process of claim 1, wherein the neurogenic niche is the subventricular zone.

6. The process of claim 1, wherein the MSCs are obtained from a human.

7. The process of claim 1, wherein the area of brain injury is in the cortex.

8. The process of claim 1 wherein 0.6% of implanted cells persist one month after implantation.

9. The process of claim 1 wherein 0.16% of implanted cells persist three months after implantation.

10. The process of claim 1, further comprising proliferation of the endogenous neurogenic cells.

11. A process wherein a pathway for cell migration is formed in the brain of a subject, wherein the subject is in need of migration of endogenous neurogenic cells from a neurogenic niche to an area of brain injury, wherein:
   (a) exogenous cells are implanted between the neurogenic niche and the area of brain injury;
   (b) the implanted exogenous cells produce the pathway for cell migration;
   (c) the implanted exogenous cells do not persist; and
   (d) the endogenous neurogenic cells migrate along the pathway from the neurogenic niche to the area of brain injury;
   wherein the exogenous cells are obtained by a process comprising:
      (i) providing a culture of MSCs,
      (ii) contacting the cell culture of step (i) with a polynucleotide comprising sequences encoding a Notch intracellular domain (NICD) wherein said polynucleotide does not encode a full-length Notch protein,
(iii) selecting cells that comprise the polynucleotide of step (ii), and
(iv) further culturing the selected cells of step (iii) in adherent culture in the absence of selection.

12. The process of claim 11, wherein the brain injury is a traumatic brain injury.

13. The process of claim 12, wherein the traumatic brain injury results from external mechanical force.

14. The process of claim 11, wherein the subject is a human.

15. The process of claim 11, wherein the neurogenic niche is the subventricular zone.

16. The process of claim 11, wherein the MSCs are obtained from a human.

17. The process of claim 11, wherein the area of brain injury is in the cortex.

18. The process of claim 11, further comprising proliferation of the endogenous neurogenic cells.

19. The process of claim 11 wherein 0.6% of implanted cells persist one month after implantation.

20. The process of claim 11 wherein 0.16% of implanted cells persist three months after implantation.

* * * * *